United States Patent [19]

Cook

[11] Patent Number: 5,445,648
[45] Date of Patent: Aug. 29, 1995

[54] STAPLES

[76] Inventor: Melvin Cook, 8 Saddle Ridge Rd., Hohokus, N.J. 07423

[21] Appl. No.: 228,058

[22] Filed: Apr. 15, 1994

Related U.S. Application Data

[63] Continuation of Ser. No. 24,501, Mar. 2, 1993, Pat. No. 5,342,396.

[51] Int. Cl.6 .............................................. A61B 17/04
[52] U.S. Cl. ..................................... 606/219; 411/457
[58] Field of Search .................. 606/219, 75; 227/901, 227/902; 411/457, 460, 470, 471

[56] References Cited

U.S. PATENT DOCUMENTS

| 4,489,875 | 12/1985 | Crawford et al. | 227/19 |
| 4,607,638 | 8/1986 | Crainich | 606/219 |
| 5,163,598 | 11/1992 | Peters et al. | 227/19 |
| 5,246,443 | 9/1993 | Mai | 606/219 |

Primary Examiner—Gary Jackson

[57] ABSTRACT

An improved surgical staple is disclosed wherein predetermined regions of the staple legs are weakened to cause bending and deformation of said legs in a controlled manner. The staple provides a uniform compression of a tissue into which it is inserted.

2 Claims, 2 Drawing Sheets

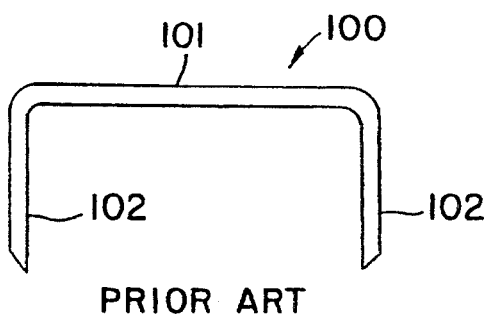
FIG. 1
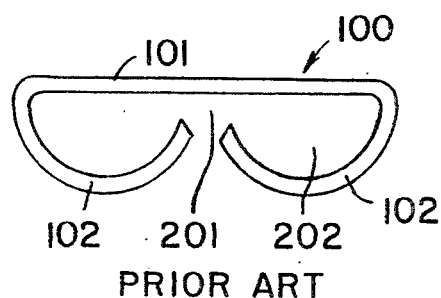
FIG. 2
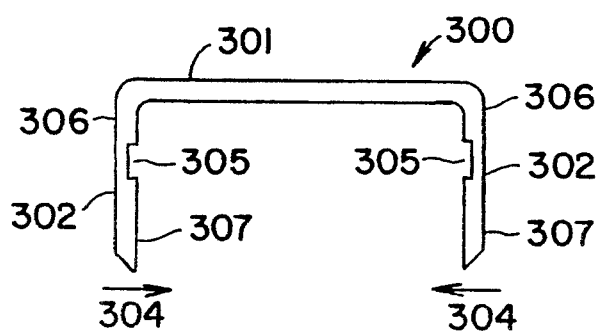
FIG. 3
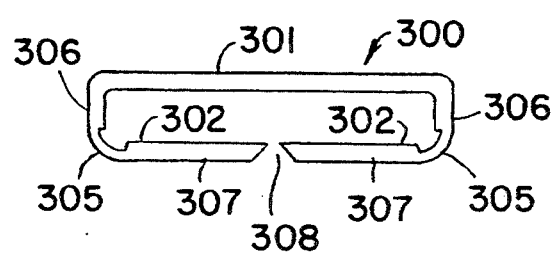
FIG. 4

FIG. 6
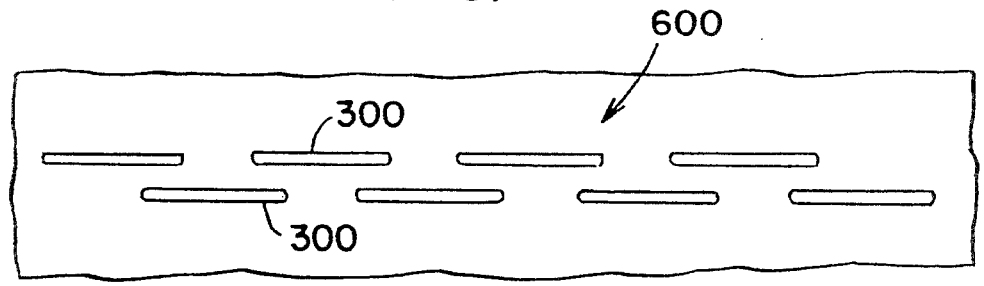

STAPLES

The present application is a rule 1.60 continuation of application Ser. No. 08/024,501 filed Mar. 2, 1993, now U.S. Pat. No. 5,342,396.

TECHNICAL FIELD

This invention relates to stapling and, more particularly, to improved staples for use in surgery and in other fields.

BACKGROUND OF THE INVENTION

Staples have a variety of uses. For example, surgeons use thin wire staples to join the cut ends of hollow organs or ducts (anastomosis) and to achieve hemostasis. Thin wire staples are made by deforming a length of thin wire with uniform cross section and material properties to a U-shape. FIG. 1 shows a common prior art thin wire staple 100, including a crown 101 and two legs 102. The staple shown in FIG. 1 has uniform cross section and material properties, except as these may be altered in the region where the staple legs join the crown during deformation of the wire to the U-shape. Surgical staples are made of materials inert to attack by body fluids, e.g., stainless steels.

When a staple is installed, its legs are pushed into the material being stapled. During installation, some staples are deformed, i.e., bent past their elastic limit to achieve a permanent change in shape.

FIG. 2 shows the staple of FIG. 1 deformed to a B-shape during installation due to its legs having being forced against an anvil with channels to direct the legs as they bend and deform. This anvil is located on the side of the material being stapled that is opposite to the side into which staple insertion is made. The deformation of the staple of FIG. 1 occurs in its leg region at and near the legs' juncture with the crown, since this is where the maximum bending stress develops.

FIG. 2 shows that the separation of different locations on the legs 102 from the crown 101 varies for a B-shaped staple. Thus, when B-shaped staples are used in surgery, tissues located between different regions of the legs and the crown undergo different compressions, and tissue compression varies in the vicinity of the gap between leg ends when these ends are not in close proximity.

To achieve hemostasis using staples, the tissue compressed least by the staples must still be compressed sufficiently for the hemostasis despite the possibility that the tissue compressed most may be perforated or damaged due to excessive compression or distortion. Necrosis, additional scar tissue formation and longer healing times can result from excessive compression or distortion. Shrinkage of scar tissue over time can lead to adverse results, and thus it is important to avoid forming more scar tissue than necessary.

If the curvature of the staple legs where they join the crown is large, i.e., if the staple has a small radius at the junctures of the legs and the crown, then the separation between the legs and the crown will be small, and tissue may undergo excessive compression. If the curvature is small, i.e., if the staple has a large radius at the junctures of the legs and the crown, then tissue distortion may be excessive in the vicinity of the junctures.

It is an object of the present invention to provide a staple which achieves uniform compression of stapled material.

It is also an object of the present invention to provide a surgical staple which minimizes scar tissue formation.

It is a further object of the present invention to provide a staple which minimizes distortion of the material stapled.

It is an additional object of the present invention to provide a surgical staple which minimizes healing time.

It is a further object of the present invention to provide a staple which minimizes damage of material stapled.

SUMMARY OF THE INVENTION

The above cited problems and others are overcome and the objects of the invention are achieved in accordance with an improved staple whose resistance to deformation in predetermined regions is so weakened that deformation during installation preferentially occurs in said predetermined regions although in the absence of such weakening deformation would not otherwise preferentially occur in said predetermined regions. Such predetermined regions with weakened resistance to deformation are hereinafter termed "deformation zones". Deformation zones may be formed by reducing the minimum moment of inertia, $I$, of the staple cross section in the deformation zone, by reducing the modulus of elasticity, $E$, of the staple material, or by mechanically supporting the staple so that maximum bending stress occurs at the point of such support.

In the preferred embodiment of the inventive staple, the staple has two legs, and each leg has a deformation zone in a predetermined region that is separated from the staple crown by a leg region with greater resistance to deformation than that of the deformation zone under the stress generated when the staple encounters an anvil during installation, so that the staple preferentially deforms in the deformation zone.

During installation, the inventive staple is, preferably, deformed to a rectangular shape with rounded corners. This helps to achieve uniform compression and to minimize distortion of the stapled material.

FIG. 1 depicts a prior art staple before installation;

FIG. 2 shows the prior art staple of FIG. 1 after being deformed to a B-shape;

FIG. 3 depicts an exemplary embodiment of the inventive staple;

FIG. 4 shows the staple of FIG. 3 after being deformed to a rectangular shape;

FIG. 6 shows a double staggered staple line;

DETAILED DESCRIPTION OF THE PREFERRED EMBODIMENTS

Figure 5A:
FIG. 5 shows exemplary cross sectional views (not to the scale of FIG. 3) of possible deformation zone and adjacent leg regions for the staple of FIG. 3.

A deformation zone is created by weakening the staple in a predetermined region so that deformation preferentially occurs in that region during staple installation. As is well-known in the art, the resistance to deformation of a region of a staple under stress is dependant on the magnitudes of its modulus of elasticity, E, in the region and the moment of inertia, I, of the minimum section including the axis around which the staple bends in the region. Reducing these quantities in a region reduces the stress needed to deform a staple in that region. It is usually easier to reduce I than E.

Deformation zones should not be formed by weakening the staple in the predetermined regions in such a manner as to result in staple failure, i.e., breakage, during staple deformation. For example, the improper use of sharp notches to form deformation zones can result in staple failure.

The legs of the inventive staple should be matched to the requirements of the material stapled. That is, the locations of the deformation zones should be matched to the thickness of the material being stapled and to the compression desired, and the staple leg lengths should be sized to bring the legs ends into close proximity. While such matching may require the availability of multiple staples, this is justifiable when the compression achieved and its uniformity are important.

FIG. 3 shows an exemplary staple 300 in accordance with the present invention. The staple 300 includes a crown 301 and two legs 302. Each leg 302 has a deformation zone 305 with weakened resistance to bending into direction 304 as compared to the resistance of leg regions 306 and 307 which lie outside of the deformation zone 305. When the staple 300 is subjected to stresses arising from forces acting in the direction 304, the legs will bend into that direction, so that bending and deformation will take place preferentially in deformation zone 305.

In FIG. 4, the staple of FIG. 3 is shown deformed into a rectangular shape. Material stapled with the staple of FIG. 3 will be under more uniform compression than is the case with the B-shaped staple of FIG. 2. FIG. 4 reveals that the location and length of deformation zone 305 and the length of the staple leg 302 are important leg parameters in obtaining a desired compression for stapled material of a particular thickness and in bringing the staple leg ends into close proximity. The length of leg region 306 between the crown 301 and the deformation zone 305 should be matched to the requirements set by the combination of the thickness of the material being stapled and the compression of this material that is desired. The length of leg region 307 between the deformation zone 305 and the leg end 308 should be selected such that the separation of the leg ends 308 of the deformed staple is minimized without interference between the leg ends 308 occurring as the staple is deformed during installation.

A comparison of FIG. 2 and FIG. 4 reveals that material stapled with the staple 300 of FIG. 3 will be less distorted and under more uniform compression than occurs with B-shaped staples.

Figure 5B:
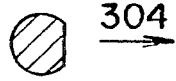
Figure 5C:
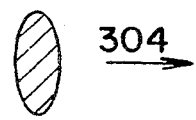

In FIG. 5, exemplary cross sections (not shown to the scale of FIG. 3) are shown for the legs 302 of the staple 300 of FIG. 3. In FIG. 5 (a), a cross section for regions of the staple legs 302 outside the deformation zone 305 is shown. In FIG. 5 (b) and (c), two different possible cross sections for the staple leg cross section in the deformation zone 305 are shown. The values of I for the staple leg in deformation zones with the cross sections shown in FIG. 5 (b) or (c) for bending into direction 304 are less than if they had the cross section of FIG. 5 (a).

In FIG. 6, a double staggered staple line 600 formed from inventive staples 300 of FIG. 4 is shown, each row being offset with respect to the other row. Surgeons make use of double staggered staple lines, e.g., to compress tissue for hemostasis at the cut end of an organ or to perform an anastomosis. The present staples thus have application in hemostasis and anastomosis, for example.

Figure 7:
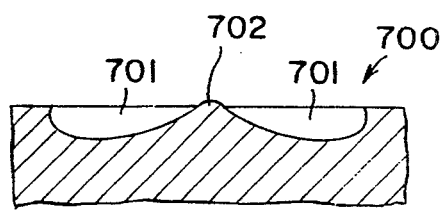
FIG. 7 is a partial front view in section of a first type of exemplary anvil.

In FIG. 7, a cross section is shown of an anvil 700 for use with the staple of FIG. 3 to produce the deformed staple of FIG. 4. Channels 701 formed in the anvil 700 direct bending and deformation of staple legs 302 when staple 300 is forced against anvil 700 and the legs 302 encounter the anvil 700. Anvil 700 is stationary as the staple 300 is forced against it.

Figure 8:
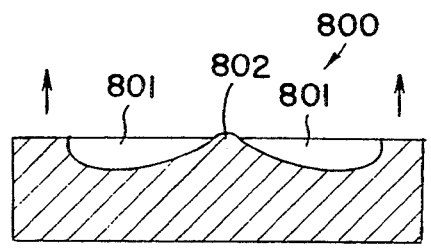
FIG. 8 is a partial front view in section of a second type of exemplary anvil.

In FIG. 8, an anvil 800 alternative to that of FIG. 7 for use with the staple 300 of FIG. 3 is shown. The legs 302 of the staple 300 encounter channels 801 of anvil 800 after penetrating through the material being stapled (not shown in FIG. 8). Anvil 800 moves towards the staple 300 as the staple 300 is forced against the anvil 800. This motion of the anvil may be accomplished using means well known to the art. The motion of the anvil minimizes distortion of the material being stapled by the staple legs 302 as they bend and deform.

It should be noted that the legs 302 after the staple 300 is deformed, as shown in FIG. 4, do not conform to the shape of the channel 701. Rather, the end 308 of leg 302 follows the shape of the channel 701 until the leg regions 306 and 307 are bent at angles (preferably, at right angles) to one another. The stapler may include a stop (702, 802) to prevent staple bending beyond the desired amount, although such a stop is not required for the installation of a staple. An exemplary stop (702, 802) is shown, but other techniques using means well known in the art can be employed to prevent the stapler jaws from closing too much so that staples are deformed beyond desired points.

Figure 9:
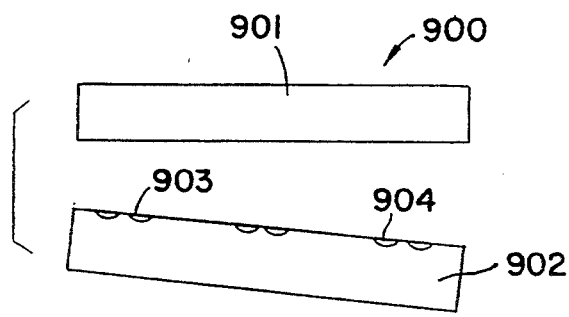
FIG. 9 is an alternative embodiment of the invention for use on material with varying thickness.

Although stapler jaws are usually parallel to each other when the thickness of the material being stapled is uniform, material thickness sometimes varies over a length where a stapler line is to be inserted. In FIG. 9, an alternative staple jaws arrangement 900 is shown which includes two stapler jaws 901 and 902 which are slanted with respect to each other. (Stapler jaw 902 functions as an anvil.) This embodiment can be used if the thickness of the material being stapled varies over the length of a line of staples that the surgeon wishes to insert.

In order to maximize the benefits of the present invention and to achieve a good result, the upper jaw 901 is slanted with respect to the lower jaw 902, as shown. As a result, the separation of the stapler jaws 901 and 902 varies in correspondence with the variation in the thickness of the material (not shown in FIG. 9) being stapled.

The individual staples used with the arrangement of FIG. 9 would have leg deformation zones located differently with respect to each other in order to accommodate the different thicknesses of the material being stapled. Specifically, it can be seen from FIG. 9 that the staple contacting channel 903 should have shorter leg lengths between its leg deformation zones and the staple crown than should the staple contacting channel 904. Additionally, the leg lengths of the staple used at channel 903 may be less than the leg lengths of the staple used at channel 904.

It is possible for the staples to be manufactured with uniform cross sections and material properties, and for the deformation zones to be formed by the surgeon by modifying the staples just prior to use so that they correspond to the requirements of the material being stapled. For example, the surgeon could notch or file the staple legs to create the deformation zones, and/or cut the staple legs to desired lengths. Devices which can be used for such purposes can use means well known in the art. Such an approach would reduce the size of staple inventory requirements.

Figure 10:
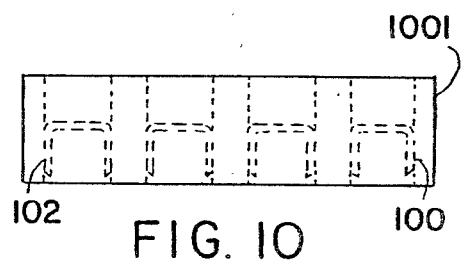
FIG. 10 depicts a loaded strip of staples for use with the invention.

FIG. 10 shows a loading strip 1001 carrying prior art staples 100. The loading strip 1001 can be placed into a device (not shown in FIG. 10) which forms deformation zones where they are desired, and which also cuts the staple legs 102 to the desired lengths. Devices which can be used for such purposes can utilize means well known in the art. The loading strip 1001 would be inserted into a suitable stapler (not shown in FIG. 10) prior to insertion of the staples 100.

Figure 11:
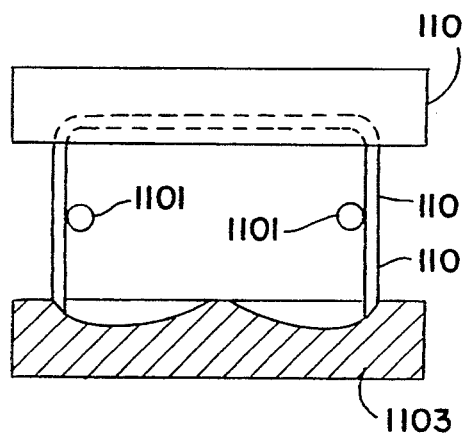
FIG. 11 shows an alternative embodiment of the present invention wherein the deformation zones are formed simultaneously with the installation of the staples.

FIG. 11 shows a still further embodiment of the invention wherein deformation zones are created as staples are inserted rather than prior to the use of the staples. The arrangement of FIG. 11 shows stapler jaws 1102, 1103 with a staple 300 located therebetween. (Stapler jaw 1103 functions as an anvil.)

Two bars 1101 are employed to form the deformation zones. The bars may be attached to the lower jaw 1103 or the upper jaw 1102. The specific technique of attaching the bars is not shown in FIG. 11 for purposes of clarity and is not material to the operation of the present invention, however means well known to the art can be used for such purpose.

Figure 12:
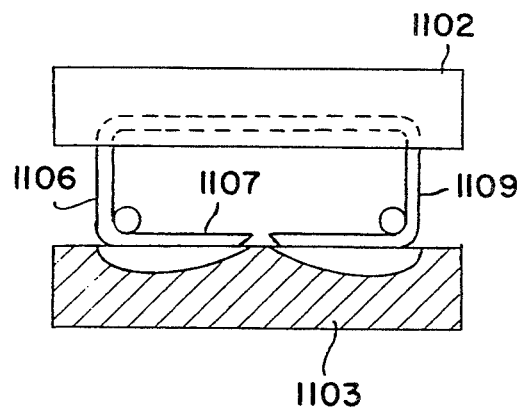
FIG. 12 shows the embodiment of FIG. 11 in use.

When the jaws 1102 and 1103 are brought towards each other, the staple 1100 will encounter the bars and bend and deform around the bags 1101. As seen in FIG. 12, the staple legs 302 will deform so that leg portions 1106 and 1107 are at angles (preferably, at right angles) to each other, just as in embodiments where deformations zones are formed prior to staple insertion.

Preferably, the anvil moves after the staple legs pass partly or completely through the material being stapled. After the staple has been deformed, the bars may move aside so that the stapler can be easily removed, or the stapler may be set up so that the stapler can slid in a direction out of the plane of FIG. 12 to disengage from the staple. Means to accomplish such disengagement are not shown, but means well known to the art can be used for such purpose.

While the disclosure has mentioned the use of these staples in surgery, it is clear that such staples can find uses in other applications, e.g., where uniform compression of the material underlying the staple is useful or where perforation of the material would be harmful.

While particular anvils have been shown, the anvil used with the inventive staple need not be one of the anvils shown but may be any means of pushing the legs towards each other to achieve the deformed shape desired and may include means for stopping staple deformation after a desired amount of deformation has occurred. Further, while staples with two legs have been described, it is obvious that the principles of the invention are applicable to staples having more than two legs, e.g., for applications where a larger area is intended to be compressed by each staple. Such modifications and/or additions which fall within the spirit and the scope of the invention are intended to be covered by the following claims.

I claim:

1. An apparatus for internal surgery comprising:
   a staple having a crown and two legs, each leg being substantially perpendicular to said crown, each leg including a tip and having a length, each leg having an elongated deformation zone, said elongated deformation zone being a region having a beginning and an end and extending along the length of said leg, said elongated deformation zone being sufficiently long that when said leg at said elongated deformation zone is deformed to a right angle said beginning and said end do not touch one another, said deformation zone also being more susceptible to bending than other regions of said less adjacent to said elongated deformation zone when said tips of said legs are forced toward each other;
   staple pusher means for pressing against the crown and thereby pushing said legs of said staples into biological tissue; and
   anvil means for exerting said forces on said tips of said legs parallel to said crown and in the direction of the other of said legs said force arising when said staple pusher means pushes said staple such that the tips of said legs penetrate through said biological tissue and against said anvil means in order to form a substantially right angle at said elongated deformation zones.

2. A staple for internal surgery comprising a crown and two legs, each leg being substantially perpendicular to said crown, each leg including a tip and having a length, each leg further having an elongated deformation zone extending along said length of said leg, each elongated deformation zone having a beginning and an end, said elongated deformation zone being more susceptible to bending than regions adjacent to said deformation zones of said legs when said tips of said legs are forced toward each other, said elongated deformation zone being sufficiently long such that said leg at said elongated deformation zone is deformed to a right angle, the beginning and the end of said deformation zone do not contact each other.

* * * * *